United States Patent [19]

Davis

[11] Patent Number: 5,013,319
[45] Date of Patent: May 7, 1991

[54] APPARATUS AND METHOD FOR CORNEA MARKING

[75] Inventor: Andrew Davis, Matawan, N.J.

[73] Assignee: Mount Sinai School of Medicine of the City University of New York, New York, N.Y.

[21] Appl. No.: 361,240

[22] Filed: Jun. 5, 1989

[51] Int. Cl.$^5$ .............................................. A61D 1/00
[52] U.S. Cl. .................................. 606/166; 128/898; 351/212; 351/205
[58] Field of Search ................ 606/166, 172; 351/206, 351/212; 128/898

[56]  References Cited

U.S. PATENT DOCUMENTS

| | | | |
|---|---|---|---|
| 4,359,941 | 11/1982 | Golubkov et al. | 606/166 |
| 4,417,579 | 11/1983 | Soloviev et al. | 606/166 |
| 4,705,035 | 11/1987 | Givens . | |
| 4,750,491 | 6/1988 | Kaufman et al. | 606/166 |
| 4,799,784 | 1/1989 | Safir . | |
| 4,844,060 | 7/1989 | Krumeich | 606/166 |
| 4,875,767 | 10/1989 | Wright | 351/212 |
| 4,880,017 | 11/1989 | Soll et al. | 128/898 |

FOREIGN PATENT DOCUMENTS 2091561 8/1982 United Kingdom .
2124494 2/1984 United Kingdom .

OTHER PUBLICATIONS

Derwent Abstract No. 85-067384/11 of U.S.S.R. Pat. No. 1,109,159.
Derwent Abstract No. 84-093797/15 of U.S.S.R. Pat. No. 1,026,084.
Derwent Abstract No. 84-074162/12 of U.S.S.R. Pat. No. 1,021,454.
Uozato, H. and Guyton, D. L., "Centering Corneal Surgical Procedures", Am. J. of Ophthalmology, vol. 103, pp. 264-275 (1987).
Steinberg, E. B. and Waring, G. O., "Comparison of Two Methods of Marking the Visual Axis on the Cornea During Radial Keratotomy", Am. J. of Ophthalmology, vol. 96, pp. 605-608 (1983).
Sanders, D. R., et al. (eds.), "Refractive Corneal Surgery", pp. 134-135 (1986).
Uozato, H. et al., "Measurement of Visual Axis Using a Laser Beam", in Breinin, G. M. and Siegel, I. M. (eds.), "Advances in Diagnostic Visual Optics", Proceedings of the Second International Symposium, Tucson, Ariz., 10/23-25/89, pp. 22-29 (1983).
Walsh, P. M. and Guyton, D. L., "Correspondence Re: Comparison of Two Methods of Marking the Visual Axis on the Cornea During Radial Keratotomy", Am. J. of Ophthalmology, vol. 97, pp. 660-661 (1984).
Bonds, A. B. and MacLeod, D. I. A., "A Displaced Stiles-Crawford Effect Associated with an Eccentric Pupil", Invest. Ophthalmol. Visual Sci., vol. 17, pp. 754-761 (1978).
Enoch, J. M. and Laties, A. M., "An Anaylsis of Retinal Receptor Orientation: II. Predication for Psychophysical Tests", Investigative Ophthalmology, vol. 10, pp. 959-970.

*Primary Examiner*—Robert Hafer
*Assistant Examiner*—Kerry Owens
*Attorney, Agent, or Firm*—Brumbaugh, Graves, Donohue & Raymond

[57] ABSTRACT

An apparatus for maintaining a patient's visual fixation and centration while marking the patient's cornea comprises a housing, a light source axially aligned and integral to the housing to maintain the patient's visual fixation and centration while the cornea is marked with the light source acting as a point source of light and enabling the patient to see a shadow image of the patient's pupil, and means for marking the cornea which are integral to the housing and positioned such that the light source and means for marking are axially aligned. A method for maintaining a patient's visual fixation and centration while marking the cornea employs the apparatus in such a manner that the patient looks directly at the center of the image emanating from the illuminated light source, which is a shadow image of the patient's pupil, and the means for marking are then employed to place a mark on the patient's cornea. The apparatus and method are advantageous in that they provide a simple and effective means of accurately marking the cornea prior to corneal surgery.

20 Claims, 4 Drawing Sheets

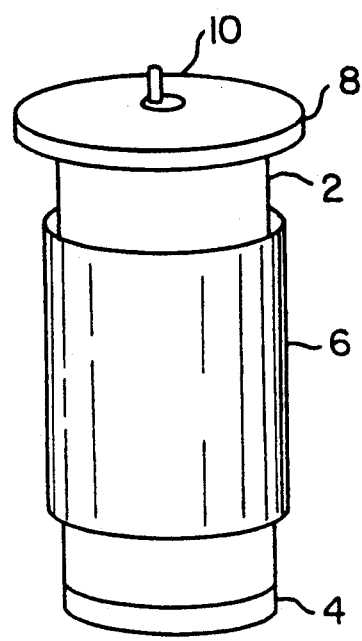
FIG. IA
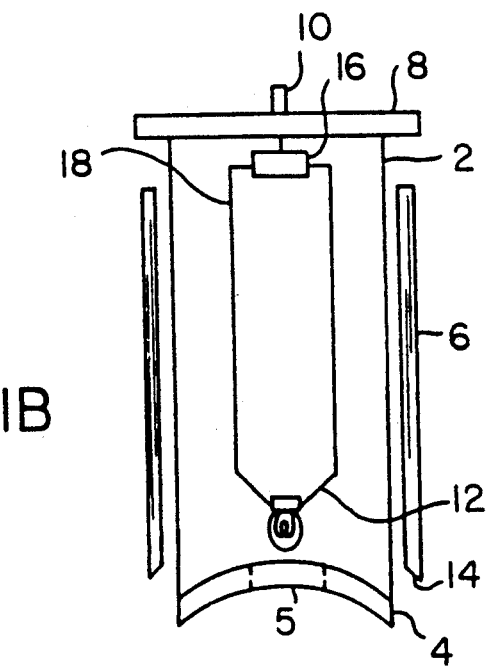
FIG. IB

APPARATUS AND METHOD FOR CORNEA MARKING

BACKGROUND OF THE INVENTION

This invention relates to an apparatus and method for marking the cornea prior to corneal surgery. More particularly, this invention relates to an apparatus and method for maintaining a patient's visual fixation and centration while marking the cornea.

Most refractive or corneal surgical procedures require proper centering on the cornea, since eccentricity of the refractive procedure may result in less than optimum visual function. To achieve the best surgical results, it is important that the corneal surgical procedure to be employed is properly centered.

Methods of marking the "center" of the cornea generally require the patient to fixate on a light or spot located on the operating microscope. Most methods use the corneal light reflex as a reference point for the surgeon to mark the cornea using an operating microscope. For example, currently used methods for centering corneal surgical procedures with an operating microscope are discussed in Uozato, U. and Guyton, D. L., "Centering Corneal Surgical Procedures," Am. J. of Ophthalmology, Vol. 103, pp. 264-75 (1987). A comparison of the use of the reflection of the operating microscope filament on the cornea surface and the use of Osher's centering device mounted on the microscope and employing a fiber optic light source is described by Steinberg, E. B. and Waring, G. O., "Comparison of Two Methods of Marking the Visual Axis on the Cornea during Radial Keratotomy," Am. J. of Ophthalmology, Vol. 96, pp. 605-08 (1983). A binocular method of aligning the eye on the visual axis for marking the center of the visual axis on the cornea using a binocular microscope is described, for example, in Sanders, D. R. et.al. (eds.), Refractive Corneal Surgery, pp. 134-35 (1986).

The apparatus and method of this invention are advantageous in that they do not necessarily require an operating microscope or any attachments affixed to the microscope to achieve accurate centering. In addition, the method and apparatus of this invention may be used for centering the cornea with greater speed and less manipulation by the surgeon.

A source of error common to all of the known methods of corneal marking is the surgeon. However, this source of error is reduced in the apparatus and method of this invention, as both are less dependent upon the alignment technique or judgment of the surgeon. This reduction of the surgeon's potential error results in the cornea being marked more accurately.

Another source of error in the known methods is due to a parallax phenomenon. This occurs when using either the corneal light reflex or the pupil for centering. However, the apparatus and method of this invention mark the cornea directly, thus eliminating this parallax error.

This invention is also advantageous in that it achieves greater accuracy over currently practiced corneal marking methods in cases where there has been extensive corneal disease since it is less dependent on a clear cornea than other methods.

SUMMARY OF THE INVENTION

This invention is directed to an apparatus and method for maintaining a patient's visual fixation and centration while marking the patient's cornea. The apparatus of this invention comprises:

a housing;

(b) a light source axially aligned and integral to the housing to maintain the patient's visual fixation and centration while the cornea is marked, the light source acting as a point source of light and enabling the patient to see a shadow image of the patient's pupil; and (c) means for making the cornea which are integral to the housing and positioned such that the light source and means for marking are axially aligned.

The method of this invention is directed to maintaining a patient's visual fixation and centration while marking the patient's cornea, the method comprising:

(a) positioning above the patient's eye an apparatus comprising:
  (i) a housing;
  (ii) a light source axially aligned and integral to the housing to maintain the patient's visual fixation and centration while the cornea is marked, the light source acting as a point source of light and enabling the patient to see a shadow image of the patient's pupil; and
  (iii) means for marking the cornea which are integral to the housing and positioned such that the light source and means for marking are axially aligned;

(b) illuminating the light source;

(c) contacting the lower portion of the housing with the patient's cornea;

(d) instructing the patient to look directly at the center of the image emanating from the light source; and (e) employing the means for marking to place a mark on the cornea.

The apparatus and method of this invention are advantageous is that they provide a simple and effective means of accurately marking the cornea prior to corneal surgery.

BRIEF DESCRIPTION OF THE DRAWINGS

FIG. 1 depicts a side view (1A) and cross-sectional view (1B) of a preferred embodiment of the apparatus of this invention.

DETAILED DESCRIPTION OF THE INVENTION

Figure 2A:
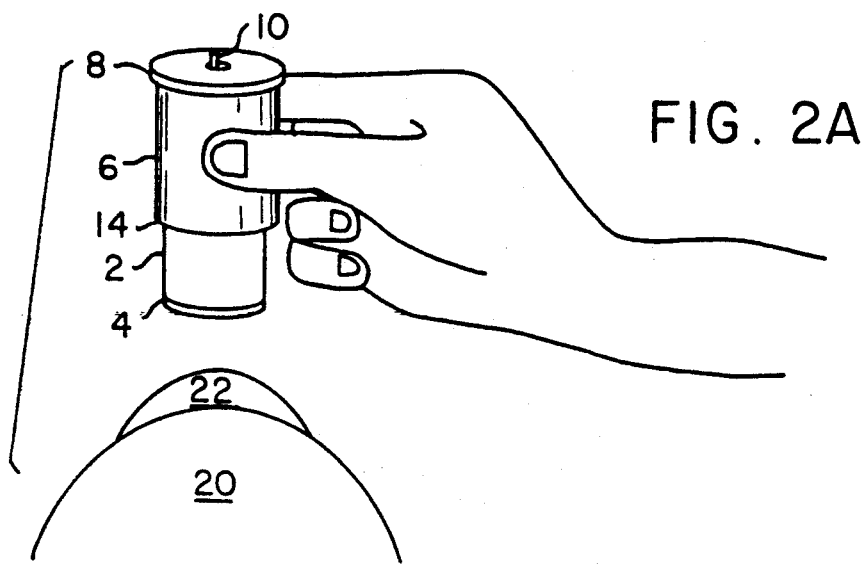
FIG. 2 depicts a preferred embodiment of the method of this invention.

This invention will become apparent from the following detailed description.

This invention is directed to an apparatus and method for maintaining a patient's visual fixation and centration while marking the patient's cornea. As used in this specification and in the appended claims, "centration" is defined such that when the patient's gaze is directed at the center of the image formed by the light source, that image being a shadow image of the patient's pupil, the means for marking the cornea are thereby aligned in such a manner that the cornea may be marked in axial alignment to the patient's pupil and line of sight.

The apparatus of this invention comprises a housing, a light source axially aligned and integral to the housing to maintain the patient's visual fixation and centration while the cornea is marked, with the light source acting as a point source of light and enabling the patient to see a shadow image of the patient's pupil, and means for marking the cornea which are integral to the housing and positioned such that the light source and means for marking the cornea are axially aligned.

The light source to be employed in this invention may be amplified or unamplified light. Lenses, mirrors, filters and the like may be used to amplify, filter or direct the light. For example, in one embodiment, the light source may be a translucent material which is illuminated by an external light source such as an operating microscope. In another embodiment, the light source is preferably selected from the group consisting of a fluorescent or incandescent lamp, a diffused laser and a light-emitting diode (LED).

It is an essential feature of this invention that the light source behaves optically as a point source of light. Thus, the positioning and size of the light source relative to the other components of the apparatus of this invention must be such that the light source behaves optically as a point source of light.

It is another essential feature of this invention that the light source is positioned integral to the housing in such a manner that the patient is able to visualize a shadow image of the patient's pupil when the light source is illuminated. It is another advantage of this invention that the above-described positioning minimizes or eliminates "decentration" (i.e. misalignment of the means for marking and the patient's pupil and line of sight) as a result of unintentional tilting or movement of the housing by the surgeon while marking the cornea.

The apparatus of this invention may additionally comprise means for powering the light source which may include an external power supply such as alternating or direct current brought to the apparatus by means of suitable wiring, or a direct current battery either affixed to or exterior to the apparatus. Means for controlling the power supply and illumination of the light source may include an electrical switch either affixed to or external to the apparatus. The switch, power supply and light source may be interconnected to achieve desired illumination and control by means of suitable wiring.

Means for marking the cornea may include sharpened edges made of metal, plastic, glass or the like which are gently pressed on the cornea surface with a force sufficient to achieve marking. The edges may preferably be circular in shape to make a circular marking, although other patterns may be used. For example, in one embodiment means for marking may be fashioned so as to make a plurality of marks, such as an inner ring and a second outer concentric ring with a number of equally spaced radial marks. In another embodiment, the means for marking the cornea may comprise means for applying a marking fluid such as ink, dye and the like to make a temporary mark on the cornea. In yet another embodiment, the means for marking may be an optical template for aligning a surgical laser used for marking the cornea.

The housing may be of any shape, and in one particularly preferred embodiment is cylindrical in shape. In another preferred embodiment, the housing has a tapered or conical lower portion. In yet another embodiment, the lower portion of the housing is concave in shape so that it may rest comfortably yet firmly on the cornea prior to and during marking. It may additionally comprise means for magnifying, directing, and filtering light emanating from the light source. The above-described embodiments of the housing may be employed separately or in combination. For example, in one particularly preferred embodiment, the apparatus of this invention comprises a cylindrical housing having a concave-shaped plate affixed to the lower end of the housing. In another embodiment, the apparatus comprises a cylindrical housing characterized by having a conical-shaped lower portion.

The method of this invention comprises:
(a) positioning above the patient's eye an apparatus comprising
  (i) a housing;
  (ii) a light source axially aligned and integral to the housing to maintain the patient's visual fixation and centration while the cornea is marked, the light source acting as a point source of light and enabling the patient to see a shadow image of the patient's pupil; and
  (iii) means for marking the cornea which are integral to the housing and positioned such that the light source and means for marking are axially aligned;
(b) illuminating the light source;
(c) contacting the lower portion of the housing with the patient's cornea;
(d) instructing the patient to look directly at the center of the image emanating from the light source; and
(e) employing the means for marking to place a mark on the cornea.

The housing, light source and means for marking are all as previously described. The sequencing of the above-described positioning, illuminating, contacting and instructing steps of the method of this invention are not critical, and may be interchanged. In one particularly preferred embodiment of the method of this invention, the patient's eye is first premedicated and anesthetized with a topical anesthetic in a manner well known to those skilled in the art. The above-described apparatus of this invention is then positioned above the patient's eye, and the light source is illuminated. The lower portion of the housing of the apparatus is then contacted with the patient's cornea, and the patient is instructed to look directly at the center of the image emanating from the light source. The means for marking the cornea, which in this embodiment comprise sharpened edges, are then gently pressed on the cornea with a force sufficient to achieve marking. The entire apparatus is then removed from the vicinity of the patient's eye.

While not wishing to be bound by any one theory, it is believed that the advantageous results of the apparatus and method of this invention are obtained because, when the apparatus of this invention is employed, the patient views a shadow image of his or her own pupil, and the patient's direction of gaze with respect to this shadow image is such that the means for marking and the patient's optical axis are axially aligned; thus a mark is made which is aligned with the patient's optical axis.

The invention will become apparent from the following detailed description of various preferred embodiments of the invention together with specific references to the accompanying figures.

FIG. 1 depicts side (FIG. 1A) and cross-sectional (FIG. 1B) views of a preferred embodiment of the apparatus of this invention. In this embodiment, as depicted in FIG. 1A, inner cylindrical tube 2 has affixed to its lower end a concave-shaped plate 4 which allows inner cylindrical tube 2 to rest on a curved corneal surface.

Outer cylindrical tube 6 is concentrically located to inner cylindrical tube 2 in such a manner that outer cylindrical tube 6 freely slides axially along the outer surface of inner cylindrical tube 2. Cap 8, having a diameter greater than the outer diameter of outer cylindrical tube 6, is affixed to the upper end of inner cylindrical tube 2, thereby preventing outer cylindrical tube 6 from sliding over the upper end of inner cylindrical tube 2. Switch 10 located on the outer portion of cap 8 is used to control power to light source 12, which is positioned within the interior portion of inner cylindrical tube 2, as shown in FIG. 1B.

FIG. 1B is a cross-sectional view of the apparatus set forth in FIG. 1A. In FIG. 1B, plate 4 is affixed to the lower end of inner cylindrical tube 2, outer cylindrical tube 6 is concentrically located to inner cylindrical tube 2 and cap 8 is affixed to the upper end of inner cylindrical tube 2, all as previously described. Plate 4, having a concentric hole 5 which is axially aligned with light source 12, is made from an opaque material. The lower end of outer cylindrical tube 6 is fashioned in such a manner that it provides a sharpened edge 14 for marking the cornea when contacted thereto. Light source 12 is positioned within the interior portion of inner cylindrical tube 2 relative to plate 4 and hole 5 such that it is axially aligned with hole 5 and behaves as a point source of light when viewed by the patient as plate 4 rests on the patient's cornea.

In this embodiment, light source 12 is a LED powered by a power source which is battery 16. Current is supplied from battery 16 to light source 12 by means of appropriate wiring 18, which is shown schematically. Control of the power of battery 16 is achieved by means of switch 10 located on the outer portion of cap 8 and integrated into the electrical circuit of light source 12, wiring 18, and battery 16.

Figure 2B:
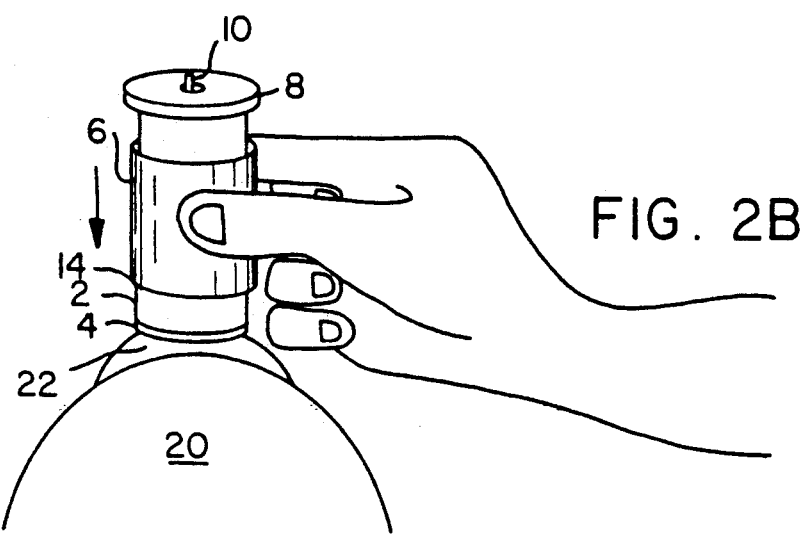
Figure 2C:
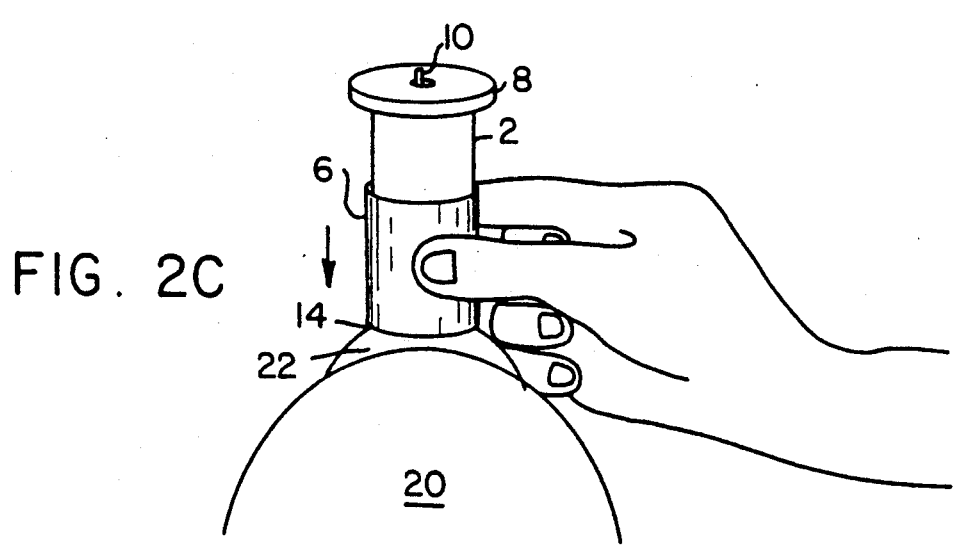

FIG. 2 depicts a preferred embodiment of the method of this invention. In this embodiment, the apparatus depicted in FIG. 1 and described above is first positioned above the patient's eye 20 and cornea 22 as shown in FIG. 2A. Light source 12 (not shown) is illuminated using switch 10 located on the outer portion of cap 8, as previously described. The apparatus is then lowered in such manner that concave-shaped plate 4 rests on cornea 22 with outer cylindrical tube 6 retracted from cornea 22, the patient's eye having been premedicated and anesthetized with a topical anesthetic. Outer cylindrical tube 6 is then lowered until the full weight of inner cylindrical tube 2 is supported by the cornea 22, as depicted in FIG. 2B. The patient is then instructed to look directly at the center of the image emanating from light source 12, which is visible to the patient through hole 5 (not shown) in plate 4. Outer cylindrical tube 6 is thereafter gently lowered as depicted in FIG. 2C until sharpened edge 14 located at the lower end of outer cylindrical tube 6 contacts cornea 22 and marks a ring on cornea 22. Outer cylindrical tube 6 is then retracted and the entire apparatus is removed from the vicinity of the patient's eye.

Figure 3:
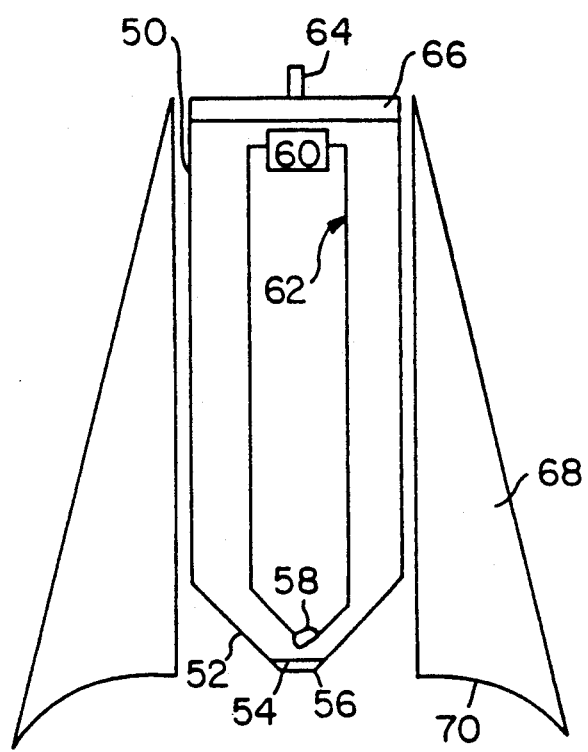
FIG. 3 depicts a cross-sectional view of another preferred embodiment of the apparatus of this invention.

FIG. 3 depicts a cross-sectional view of another embodiment of the apparatus of this invention. In this embodiment, cylindrical housing 50 has a conical-shaped lower end 52 which further comprises a tip portion 54 which is at least partially transparent and has integral to it sharpened marking edges 56 for marking the cornea when contacted thereto. Light source 58 in this embodiment is a LED supplied with current for illumination through wiring 62, the power supplied by battery 60 which in turn is controlled by switch 64 which is located on the outer portion of cover plate 66 affixed to housing 50. An optional cylindrical guide 68 allows housing 50 to be lowered therethrough so that guide 50 and housing 68 are axially aligned. Guide 68 has a concave-shaped lower end 70 which allows the guide to rest on a curved corneal surface.

One embodiment of the method of this invention employing the apparatus depicted in FIG. 3 is as follows. Housing 50 is first positioned above the patient's eye. Light source 58 is illuminated by use of switch 64 which causes current from battery 60 to be supplied to light source 58 through wiring 62. The patient's eye having been pretreated and anesthetized as previously described, housing 50 is then lowered in such a manner that tip portion 54 and marking edges 56 rest on the cornea. The patient is then instructed to look directly as the center of the image emanating from light source 58, and housing 50 is gently pushed downward in such a manner that edges 56 mark a ring on the cornea. Housing 50 is then removed from the vicinity of the patient's eye.

Another embodiment of the method of this invention employing the apparatus depicted in FIG. 3 is as follows. Housing 50 and guide 68 are first positioned above the patient's eye. Light source 58 is illuminated by use of switch 64 which causes current from battery 60 to be supplied to light source 58 through wiring 62. The apparatus is then lowered in such a manner that lower end 70 of guide 68 rests on the patient's cornea with tip 54 of housing 50 retracted from the cornea. The patient's eye having been pretreated and anesthetized as previously described, housing 50 is then lowered through guide 68 in such a manner that tip portion 54 and marking edges 56 rest on the cornea. The patient is then instructed to look directly at the center of the image emanating from light source 58, and housing 50 is then gently pushed downward in such a manner that edges 56 mark a ring on the cornea. Housing 50 is then retracted and the entire apparatus is removed from the vicinity of the patient's eye.

Figure 4A:
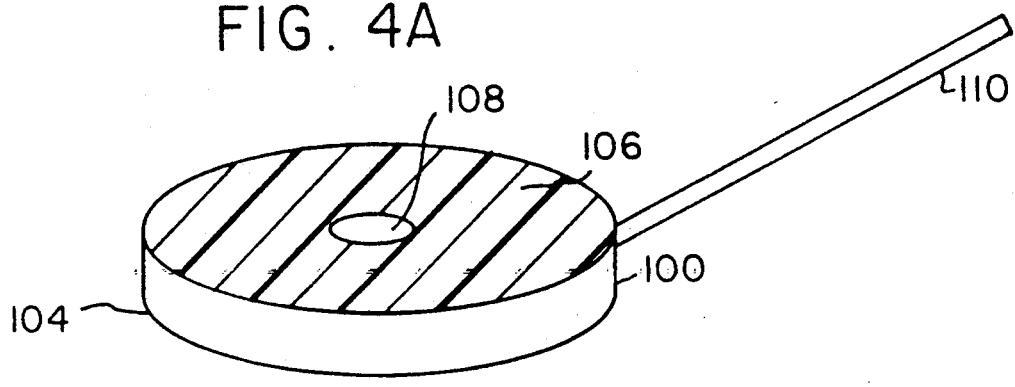
FIG. 4 depicts an isometric side view (4A), cross-sectional view (4B) and bottom view (4C) of another preferred embodiment of the apparatus of this invention.
Figure 4B:
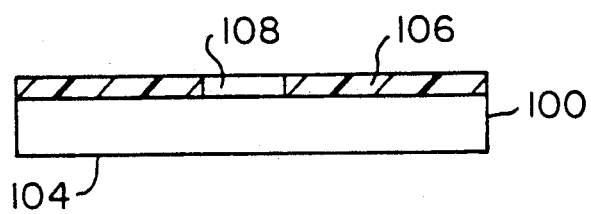
Figure 4C:
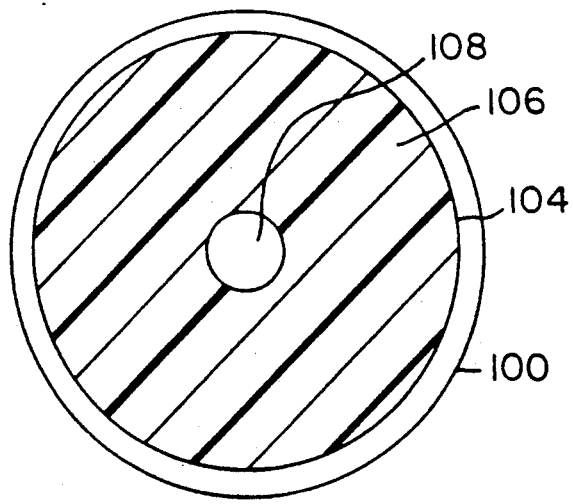

FIG. 4 depicts an isometric side view (FIG. 4A), cross-sectional view (FIG. 4B) and bottom view (FIG. 4C) of another embodiment of the apparatus of this invention. The apparatus comprises cylindrical housing 100 having means for marking the cornea which are sharpened marking edges 104 integral to the lower end of housing 100. Covering 106, which is opaque, covers the upper end of housing 100 and has a translucent material 108 centrally located therein in such a manner that the centers of translucent material 108, housing 100, and means for marking 104 are axially aligned. In FIG. 4, translucent material 108 is circular in shape and integral to opaque covering 106. In other embodiments, differently shaped translucent materials may be employed. A handle 110 (not shown in FIGS. 4B and 4C) may optionally be employed by the surgeon to position the apparatus and aid in marking the cornea.

An alternate embodiment of the method of this invention employing the apparatus set forth in FIG. 4 and described above is as follows. Housing 100 is positioned by means of handle 110 above the patient's eye, and covering 106 is illuminated by an external source such as an operating microscope in such a manner that light passes through translucent material 108 located therein. Housing 100 is then lowered by means of handle 110 in such a manner that its lower end including sharpened marking edges 104 rest directly on the patient's cornea, the patient's eye having been pretreated and anesthetized as previously described. The patient is then instructed to look directly at the center of the image emanating from illuminated translucent material 108, with illuminated translucent material 108 acting as a point source of light. Housing 100 is then gently pushed downward using handle 110 in such a manner that marking edges 104 mark a ring on the cornea. The entire apparatus is then removed from the vicinity of the patient's eye.

Although this invention has been illustrated by reference to specific embodiments, it will be apparent to those skilled in the art that various changes and modifications may be made which clearly fall within the scope of this invention.

I claim:

1. An apparatus for maintaining a patient's visual fixation and centration while marking the patient's cornea, comprising:
   (a) a first housing;
   (b) a light source axially aligned and integral to the first housing to maintain the patient's visual fixation and centration while the cornea is marked, the light source acting as a point source of light and enabling the patient to see a shadow image of the patient's pupil; and
   (c) a second housing coaxial with the first housing having means for marking the cornea which are integral to the second housing and positioned such that the light source and means for marking are axially aligned.

2. An apparatus according to claim 1, in which the light source is selected from the group consisting of an illuminated translucent material, a fluorescent or incandescent lamp, a diffused laser and a light-emitting diode.

3. An apparatus according to claim 1, which additionally comprises means for providing and controlling power to the light source.

4. An apparatus according to claim 1, in which the means for marking the cornea are sharpened edges which are integral to and coaxial with the second housing.

5. An apparatus according to claim 1, in which the means for marking the cornea comprise means for applying a marking fluid selected from the group consisting of ink and dye on the cornea.

6. An apparatus according to claim 1, in which the means for marking the cornea comprise an optical template for aligning a surgical laser to mark the cornea.

7. An apparatus according to claim 1, which additionally comprises means for resting at least a portion of the apparatus on a curved corneal surface prior to marking the cornea.

8. An apparatus according to claim 1, comprising:
   (a) an inner cylindrical tube;
   (b) a concave-shaped plate affixed to the lower end of the inner cylindrical tube allowing the inner cylindrical tube to rest on a curved corneal surface, at least a portion of the plate being transparent;
   (c) a light source axially positioned above the concave-shaped plate within the inner cylindrical tube in such a manner that it acts as a point source of light;
   (d) means for providing and controlling power to the light source;
   (e) an outer cylindrical tube concentrically located to the inner cylindrical tube in such a manner that the outer cylindrical tube freely slides axially along the outer surface of the inner cylindrical tube;
   (f) means for mark the lower portion of the outer cylindrical tube; and
   (g) means for preventing the outer cylindrical tube from sliding over the upper end of the inner cylindrical tube.

9. An apparatus according to claim 8, in which the lower portion of the outer cylindrical tube has a sharpened circular edge for marking the cornea when contacted thereto.

10. An apparatus according to claim 8, in which a cap having a diameter greater than the outer diameter of the outer cylindrical tube is affixed to the upper end of the inner cylindrical tube, to prevent the outer cylindrical tube from sliding over the upper end of the inner cylindrical tube.

11. An apparatus according to claim 1, in which the housing further comprises a conical-shaped lower end having a tip portion which is at least partially transparent and which has integral to it sharpened marking edges for marking the cornea.

12. An apparatus according to claim 11, additionally comprising a guide having a concave-shaped lower end which allows the guide to rest on a curved corneal surface and a hollow center into which the housing is positioned in such a manner that the guide and housing are axially aligned.

13. An apparatus according to claim 1, comprising:
   (a) a cylindrical housing;
   (b) means for marking the cornea integral to the lower end of the housing; and
   (c) an opaque covering which covers the upper end of the housing and has a translucent material located therein in such a manner that the centers of the translucent material, housing, and means for marking are axially aligned.

14. An apparatus according to claim 13, in which the cylindrical housing additionally comprises a concave-shaped lower end allowing the housing to rest on a curved corneal surface.

15. An apparatus according to claim 13, in which a handle is affixed to the outer surface of the housing.

16. A method for maintaining a patient's visual fixation and centration while marking the patient's cornea, comprising:
   (a) positioning above the patient's eye an apparatus comprising
      (i) a first housing;
      (ii) a light source axially aligned and integral to the first housing to maintain the patient's visual fixation and centration while the cornea is marked. the light source acting as a point source of light and enabling the patient to see a shadow image of the patient's pupil; and
      (iii) a second housing coaxial with the first housing having means for making the cornea which are integral to the housing and positioned such that the light source and means for marking are axially aligned;
   (b) illuminating the light source;
   (c) contacting the lower portion of the first housing with the patient's cornea;
   (d) instructing the patient to look directly at the center of the image emanating from the light source; and
   (e) employing the means for marking to place a mark on the cornea.

17. A method according to claim 16, comprising:

(a) positioning above the patient's eye an apparatus comprising
   (i) an inner cylindrical tube;
   (ii) a concave-shaped plate affixed to the lower end of the inner cylindrical tube allowing the inner cylindrical tube to rest on a curved corneal surface, at least a portion of the plate being transparent;
   (iii) a light source axially positioned above the concave-shaped plate within the inner cylindrical tube in such a manner that it acts as a point source of light;
   (iv) means for providing and controlling power to the light source;
   (v) an outer cylindrical tube concentrically located to the inner cylindrical tube in such a manner that the outer cylindrical tube freely slides axially along the outer surface of the inner cylindrical tube;
   (vi) means for marking the cornea integral to the lower portion of the outer cylindrical tube; and
   (vii) means for preventing the outer cylindrical tube from sliding over the upper end of the inner cylindrical tube;
(b) illuminating the light source;
(c) positioning the apparatus in such a manner that the concave-shaped lower end of the inner cylindrical tube rests on the cornea with the outer cylindrical tube retracted from the cornea;
(d) instructing the patient to look directly at the center of the image emanating from the light source;
(e) pushing the outer cylindrical tube downward until the lower end of the outer cylindrical tube contacts and places a mark on the cornea.

18. A method according to claim 16, comprising:
(a) positioning above the patient's eye an apparatus comprising
   (i) a housing having a conical-shaped lower end further comprising means for marking the cornea;
   (ii) a light source axially positioned within the housing above the means for marking in such a manner that the light source acts as a point source of light;
   (iii) means for providing and controlling power to the light source;
(b) illuminating the light source;
(c) positioning the apparatus in such a manner that the tip portion rests on the cornea;
(d) instructing the patient to look directly at the center of the image emanating from the light source; and
(e) placing a mark on the cornea.

19. A method according to claim 16, comprising:
(a) positioning above the patient's eye an apparatus comprising
   (i) a housing having a lower end further comprising means for marking the cornea;
   (ii) a light source axially positioned within the housing above the means for marking in such a manner that the light source acts as a point source of light;
   (iii) means for providing and controlling power to the light source; and
   (iv) a guide having a concave-shaped lower end which allows the guide to rest on a curved corneal surface and a hollow center into which the cylindrical housing is positioned in such a manner that the guide and housing are axially aligned;
(b) illuminating the light source;
(c) positioning the apparatus in such a manner that the lower end of the guide rests on the cornea with the lower portion of the housing retracted from the cornea;
(d) lowering the housing in such a manner that the lower portion of the housing rests on the cornea;
(e) instructing the patient to look directly at the center of the image emanating from the light source;
(f) placing a mark on the cornea.

20. A method according to claim 16, comprising:
(a) positioning above the-patient's eye an apparatus comprising
   (i) a cylindrical housing;
   (ii) means for marking the cornea integral to the lower end of the housing; and
   (iii) an opaque covering which covers the upper end of the housing and having a translucent material located therein in such a manner that the centers of the translucent material, housing and means for marking the cornea are axially aligned;
(b) illuminating the outer surface of the covering in such a manner that light passes through the translucent material, the translucent material thereby acting as a point source of light;
(c) positioning the apparatus in such a manner that the lower end of the housing rests on the cornea;
(d) instructing the patient look directly at the center of the image emanating from the illuminated translucent material; and
(e) placing a mark on the cornea.

* * * * *

UNITED STATES PATENT AND TRADEMARK OFFICE
CERTIFICATE OF CORRECTION

PATENT NO. : 5,013,319

DATED : May 7, 1991

INVENTOR(S) : Andrew Davis

It is certified that error appears in the above-identified patent and that said Letters Patent is hereby corrected as shown below:

Col. 2, line 3, "a housing;" should read --(a) a housing;--;
Col. 2, line 10, "making" should read --marking--;
Col. 6, line 17, "as" should read --at--;
Col. 8, line 3, "mark" should read --marking the cornea integral to--;
Col. 8, line 57, "making" should read --marking--;
Col. 9, line 33, "source;" should read --source; and--;
Col. 9, line 48, "light;" should read --light; and--;
Col. 10, line 30, "source;" should read --source; and--.
Col. 10, line 49, "look" should read --to look--.

Signed and Sealed this

Tenth Day of November, 1992

*Attest:*

DOUGLAS B. COMER

*Attesting Officer*  *Acting Commissioner of Patents and Trademarks*